(12) United States Patent
Moller et al.

(10) Patent No.: US 6,613,578 B1
(45) Date of Patent: Sep. 2, 2003

(54) ACTIVATING FILM FOR CHEMILUMINESCENT ASSAYS AND METHODS FOR USE

(75) Inventors: Uwe Moller, Berlin (DE); Derek Levison, Jackson, NJ (US); Stuart Levison, Jackson, NJ (US)

(73) Assignee: EMP Biotech GmbH, Berlin (DE)

( * ) Notice: Subject to any disclaimer, the term of this patent is extended or adjusted under 35 U.S.C. 154(b) by 0 days.

(21) Appl. No.: 09/913,653

(22) PCT Filed: Feb. 16, 2000

(86) PCT No.: PCT/US00/03863
§ 371 (c)(1),
(2), (4) Date: Jun. 4, 2002

(87) PCT Pub. No.: WO00/49406
PCT Pub. Date: Aug. 24, 2000

Related U.S. Application Data
(60) Provisional application No. 60/120,125, filed on Feb. 16, 1999.

(51) Int. Cl.[7] ................................................ G01N 21/76
(52) U.S. Cl. ......................... 436/172; 422/52; 422/61; 250/361 C
(58) Field of Search ..................... 422/52, 61; 436/172, 436/531, 86, 94; 250/361 C

(56) References Cited

U.S. PATENT DOCUMENTS

| | | | |
|---|---|---|---|
| 4,411,985 A | * 10/1983 | Morrow et al. | ............. 430/352 |
| 5,386,017 A | 1/1995 | Schaap | |
| 5,516,636 A | 5/1996 | McCapra | |
| 5,709,994 A | 1/1998 | Pease et al. | |
| 5,795,987 A | 8/1998 | Schaap et al. | |
| 5,837,194 A | 11/1998 | Potter et al. | |
| 6,093,529 A | * 7/2000 | Tsuzuki et al. | ............. 430/619 |

OTHER PUBLICATIONS

Schubert et al., *Non–Radioactive Detection of Oligonucleotide Probes by Photochemical Amplification of Dioxetanes*, Nucleic Acids Research, 1995, vol. 23, No. 22, Oxford University Press.

Mansfield, et al., *Nucleic Acid Detection Using Non–Radioactive Labelling Methods*, Molecular and Cellular Probes (1995) vol. 9, No. 3, 145–156, Academic Press Limited.

* cited by examiner

*Primary Examiner*—Jeffrey Snay
(74) *Attorney, Agent, or Firm*—Hoffmann & Baron, LLP

(57) ABSTRACT

The present invention relates to chemiluminescent assays which incorporate a second film or membrane which includes a solid chemical component for activation of a stable dioxetane. Decomposition of the stable dioxetane can be accomplished using a combination of heat and chemical treatment.

58 Claims, 5 Drawing Sheets

ACTIVATING FILM FOR CHEMILUMINESCENT ASSAYS AND METHODS FOR USE

This application is a national stage application of PCT/US00/03863, filed Feb. 16, 2000, which claimed benefit of provisional application Serial No. 60/120,125, filed Feb. 16, 1999.

FIELD OF THE INVENTION

The present invention relates to chemiluminescent assays which incorporate a second film or membrane which includes a solid chemical component for activation of a stable dioxetane. Decomposition of dioxetane can be accomplished using heat and chemical treatment.

BACKGROUND OF RELATED TECHNOLOGY

Recently a variety of non-isotopic labeling methods have been developed to replace radioactive labels in DNA probe-based assays. It is most common in such methods to use marker enzymes to detect nucleic acid probes using either colormetric, chemiluminescent, bioluminescent or fluorescent methods. Each of these methods have been used reliably for both hybridization of DNA probe-based assays for nucleic acid detection as well as in solid-phase immunochemical assays wherein the target molecule is typically an antigen of interest.

Regardless of the type of non-isotopic detection method used, the labels are measured directly with fluorophores (without use of enzymes) or indirectly using enzyme amplification schemes. Wherein the label is detected directly without an enzymatic reaction, sensitivity is generally less. Typically, in an indirect labeling scheme, a label is incorporated into the probe or the analyte in the form of a small molecule such as digoxigenin, fluorescein or biotin. This label may or may not be detectable on its own and its presence is revealed using enzyme conjugates that specifically bind to the small molecule in the probe. A clear advantage of an indirect labeling scheme is the increased sensitivity one achieves through enzymatic amplification of the signal. However, a disadvantage of such methods as they are currently practiced in the field is that many steps are required in the assay protocol, requiring more time to complete the assay. Moreover, a greater number of reagents are required which means greater cost. In addition, where the method of detection is enzyme-based, stability of the enzyme and its shelf life need to be considered if one is to expect optimum performance of the assay.

Chemiluminescence detection relies on a chemical reaction that generates light. It is this method which is now widely used for both nucleic acid detection as well as solid-based immunodetection due to its high sensitivity and wide variety of analysis methods ranging from manual film reading to instrumentation for processing images. One non-radioactive detection method now commercially available is the DIG-system (Boehringer-Mannheim) which uses digoxigenin, a small molecule, as a label for a probe. After binding of a DIG-labeled probe to a target molecule, an anti-DIG antibody conjugated to the enzyme alkaline phosphatase is added. Detection is achieved through the enzymatic dephosphorylation of a 1,2-dioxetane substrate which leads to the production of a chemiluminescent signal. This method relies on an enzymatic means of amplification of the signal and as such presents a disadvantage in that considerations regarding the stability of the enzyme and its shelf life are important. In addition, several steps are required in the protocol, including the binding of a probe to an enzyme-conjugated antibody. The shelf life of an antibody is an additional consideration.

In view of the simplicity of chemical reactions relative to enzymatic reactions, it would be desirable to achieve chemiluminescent signal amplification by chemical as opposed to enzymatic means. U.S. Pat. No. 5,516,636 to McCapra and a later publication by Schubert (Nucleic Acids Research, 1995, Vol. 23, No. 22 p. 4657) describe the use of sensitizer-labeled oligonucleotide probes for the detection of nucleic acid target molecules. In a solid phase DNA probe assay, a DNA target molecule is bound to a membrane and hybridized to a sensitizer-labeled oligonucleotide complementary in sequence to the target DNA. The membrane is subsequently treated with an olefin solution. Upon exposure of the membrane to ambient oxygen and light, the sensitizer molecules become excited and transfer their excess energy to ambient oxygen for formation of singlet oxygen. The singlet oxygen therein produced reacts with the olefin on the membrane to form a stable 1,2-dioxetane in the area of the hybridization zone which when subsequently exposed to heat, chemical treatment or enzymatic treatment decomposes to emit light. Thus, oligonucleotides labeled with sensitizer are able to amplify the dioxetane concentration based on repeated excitation/oxygen quenching cycles to achieve a high level of sensitivity.

McCapra discloses that wherein the dioxetane contains a phenolic hydroxyl protecting group the triggering chemical mechanism for decomposition is the raising of pH. However, he fails to disclose particular bases suitable for the decomposition or the exact method by which it can be accomplished.

Schubert uses chemical treatment of a thermally stable dioxetane as a means of decomposing the dioxetane wherein decomposition is achieved by a change of pH using a liquid triggering solution of tetrabutyl ammonium hydroxide. While an advantage of chemical treatment includes speed and efficiency, a disadvantage of the method of Schubert lies in the use of a liquid base solution which can be caustic, inconvenient and messy to use. Schubert discloses that deprotonation via base treatment of the phenolic hydroxyl protecting group of the dioxetane used causes it to lose its thermal stability and decay with accompanying emission of light.

The prior art fails to teach the combined use of heat and chemical treatment as a means of decomposing dioxetane. It would seem therefore that there is a need for a method that could allow for the combined use of heat and chemical treatment as the triggering means for an even greater enhancement of decomposition of a stable dioxetane. Thus, if decomposition of the dioxetane acts as the bottleneck for production of a signal, it is important that the conditions under which decomposition occur be optimal. Combining chemical treatment with heat would allow for this. However, up until now it has not been possible to use both chemical treatment and heat. Heating a caustic solution of base to at or near boiling temperatures would be both dangerous and impractical.

There is therefore a need for a method of providing a chemical triggering agent in a dry form which upon exposure to an appropriate energy source such as heat can be activated for enhanced decomposition of a thermally stable dioxetane and a resultant enhancement of the chemiluminescent signal. It would be a further advantage to provide for a way to use a similar dry agent to trigger dioxetane decomposition for use in both solid-phase immunoassays and nucleic acid assays.

SUMMARY OF THE INVENTION

Figure 1:
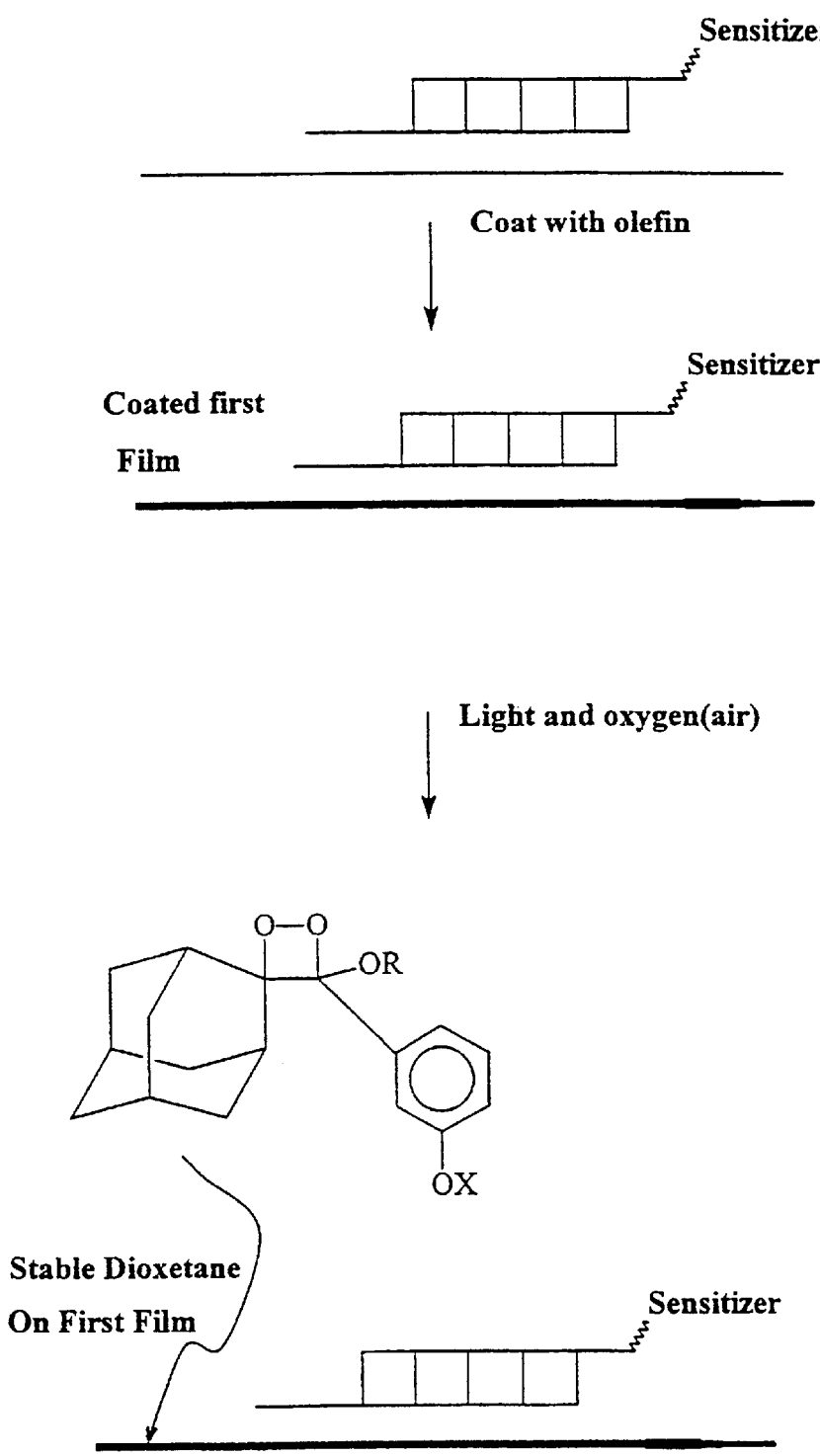
FIG. 1 is a schematic diagram showing preparation of the first film of the present invention used for nucleic acid chemiluminescent detection.

The present invention overcomes the disadvantages of currently practiced methods for chemical decomposition of dioxetanes discussed above. The present invention fulfills the need for a method by which a chemical triggering agent and heat can be combined for enhanced decomposition of a thermally stable dioxetane and a resultant enhancement of a chemiluminescent signal.

In one aspect of the present invention there is provided a film for use in chemiluminescent assays which includes a solid chemical component immobilized thereon or impregnated therein. The solid chemical component when acted upon by an energy source releases an activating substance which in the presence of a chemiluminescent precursor compound reacts therewith to produce a chemiluminescent signal for the detection of a target molecule. This film is used in the inventive assays along with another film having the target molecule and sensitizer/probe hybridized thereto.

In another aspect of the invention there is provided a chemiluminescent assay which includes a first and a second solid chemical component immobilized on or impregnated within film which when acted upon by an energy source together allow for release of an activating substance at a pH sufficient to produce a chemiluminescent signal upon reaction of said activating substance with a chemiluminescent precursor compound. Moreover, the invention involves specific binding chemiluminescent assays for the detection of target molecules wherein the target molecules can be nucleic acid or protein molecules.

In the assay, a probe is provided having a sensitizer as a label. The probe is capable of specifically binding to a target molecule in a sample undergoing the assay. Following binding of the target molecules to a first film, detection is carried out via hybridization with a sensitizer labeled probe to form a solid film-bound complex. The first solid film-bound complex is separated from unbound probe and exposed to an olefin reagent. Subsequent exposure of the first film to light of a specific wavelength range promotes the sensitizer to an excited state where it can transfer its excess energy to ambient molecular oxygen, with resultant formation of singlet oxygen. The singlet oxygen reacts with the olefin reagent to form a stable chemiluminescent precursor compound. The method of using the inventive assay includes the steps of contacting a first film, on which is formed a stable chemiluminescent precursor compound, with a second film having a solid chemical component or components immobilized or impregnated therein; and exposing said second film to an energy source which results in the release from the second film of an activating substance, which activating substance in the presence of the stable chemiluminescent precursor compound on the first film reacts to produce a chemiluminescent signal for the detection of target molecules.

A method of preparing the specific binding chemiluminescent assay of the present invention is described in the present invention. This method includes the steps of: (1) providing a first film having bound thereon target molecules, wherein said bound target molecules have been subjected to a pre-hybridization or blocking buffer solution under temperatures suitable for a chosen probe and wherein said film is further incubated with hybridization solution containing said probe under conditions suitable to bind said probe and wherein said film is subsequently exposed to an olefin solution; (2) Providing a second film by immobilizing on or impregnating therein at least one solid chemical component which when acted upon by an energy source releases an activating substance and further which in the presence of a chemiluminescent precursor compound reacts therewith to produce chemiluminescent signal for the detection of a target molecule; (3) positioning said first and second films in overlapping contact with each other to permit release of an activating substance from said second film and reaction with said chemiluminescent precursor compound on said first film to result in a detectable chemiluminescent signal.

Moreover, a kit for performing the specific binding chemiluminescent assay for use in both nucleic acid binding assays as well as immuno-assays is described. This kit includes: (1) a first film for binding of a target molecule thereon; (2) a second film comprising at least one solid chemical component immobilized on or impregnated within said film, which chemical component when acted upon by an energy source releases an activating substance which in the presence of a chemiluminescent precursor compound reacts therewith to produce a chemiluminescent signal for the detection of a target molecule.

A method of detecting target molecules using chemiluminescence is also provided and includes the steps of: (a) providing a first film having a complex comprising a target molecule bound to a sensitizer labeled probe; (b) providing a second film comprising at least one solid chemical component immobilized on or impregnated on said film, which chemical component when acted upon by an energy source releases an activating substance which in the presence of a chemiluminescent precursor compound reacts therewith to produce a chemiluminescent signal for the detection of a target molecule; (c) contacting said complex with an olefin reagent to place said complex and said olefin reagent in reactive proximity to each other; (d) exposing said complex to light and oxygen to create a chemiluminescent precursor compound; (e) contacting said first film with said second film and allowing said second film to be acted upon by an energy source to allow release from said second film of an activating substance which in the presence of said chemiluminescent precursor compound reacts to produce a chemiluminescent signal for the detection of said target molecules; and (f) detecting and/or recording said resultant chemiluminescent signal.

DETAILED DESCRIPTION OF THE INVENTION

In one aspect of the invention there is included a film for use in the detection of target molecules via chemiluminescent solid-phase and gel-type assays. The film includes a solid chemical component immobilized on or impregnated within the phase which when acted upon by an energy source releases an activating substance, which substance in the presence of a chemiluminescent precursor compound reacts therewith to produce a chemiluminescent signal for the detection of a target molecule.

The target molecule may be a nucleic acid, such as RNA or DNA. In addition, the film and its method of use may be used in solid-phase immunoassays in which the target molecule can be either antibody or antigen and wherein the corresponding sensitizer-labeled probe may be antigen or antibody, respectively. In the context of this invention, use of the term "film" includes membranes, filter paper and gels. Films may be of any useful thickness or porosity depending on their specific application. Such films are inclusive of but not limited to textile films, paper films, cellulose films, polyacrylamide and agarose gels. In particular, it is envisioned that nylon, nitrocellulose, or PVDF membranes or filter paper may be used for the release and transfer of the activating substance necessary for the chemiluminescent reaction to occur.

Figure 2:
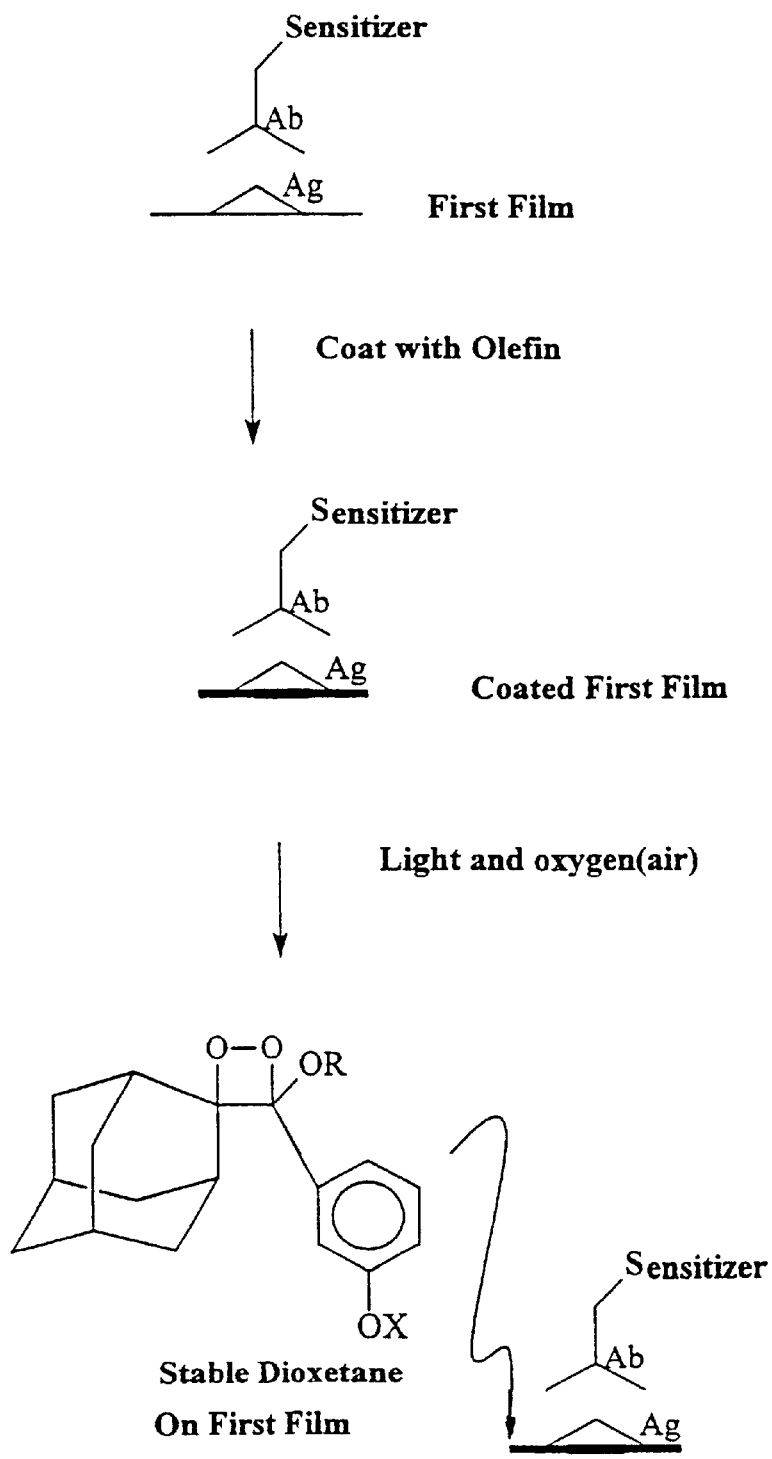
FIG. 2 is a schematic diagram showing preparation of the first film of the present invention used for antigen chemiluminescent detection.
Figure 3:
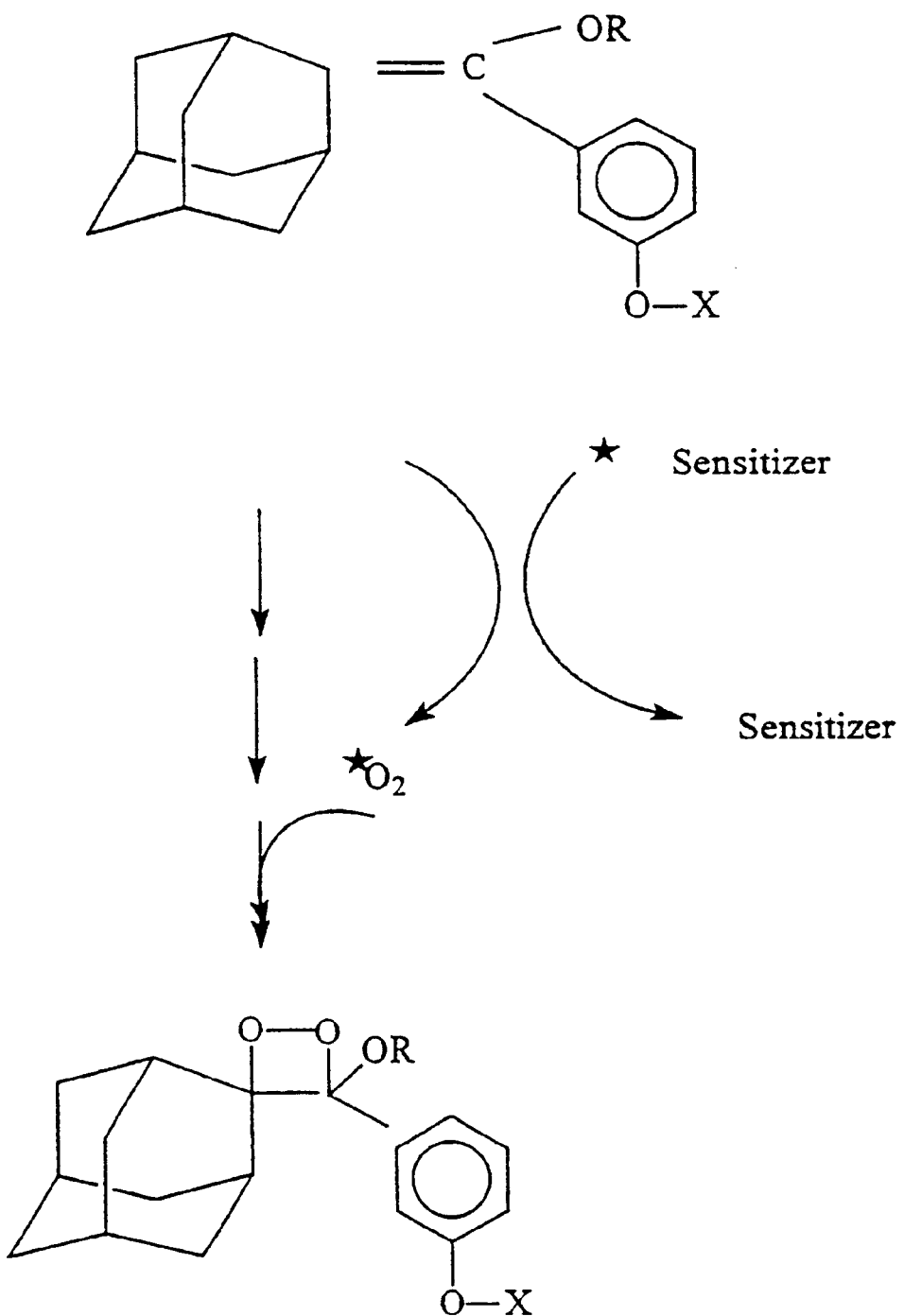
FIG. 3 is a schematic diagram showing the conversion of an olefin, used for coating the film on which the target molecule is bound, for formation of a stable 1,2-dioxetane chemiluminescent precursor.
Figure 4:
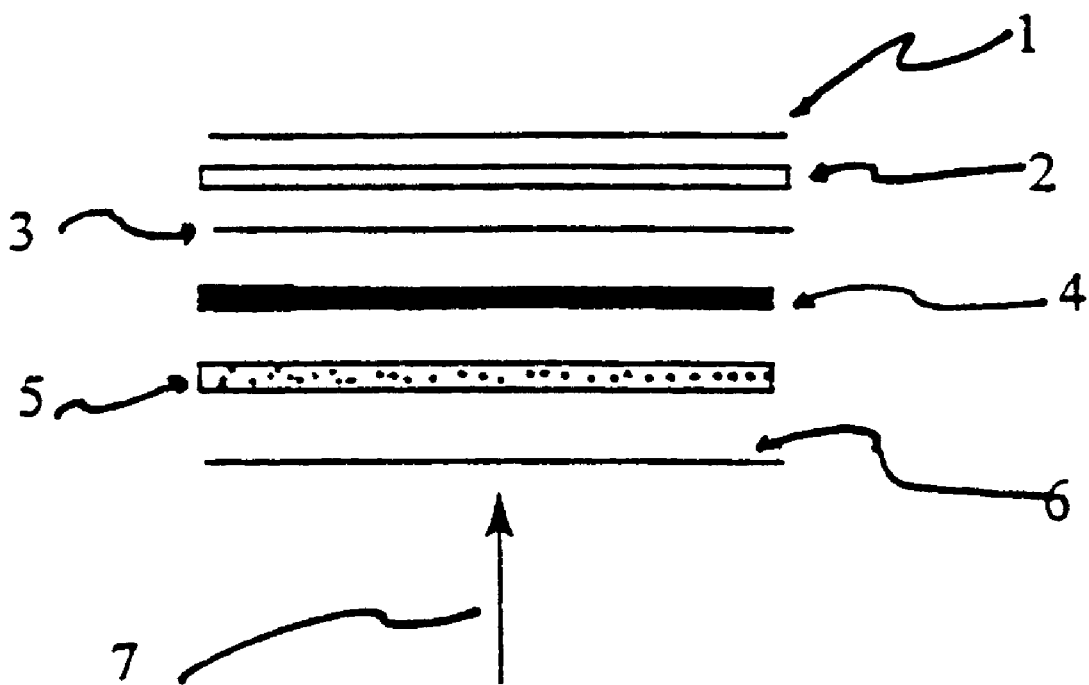
FIG. 4 is a perspective of a sandwich format of an assay of the present invention.
Figure 5:
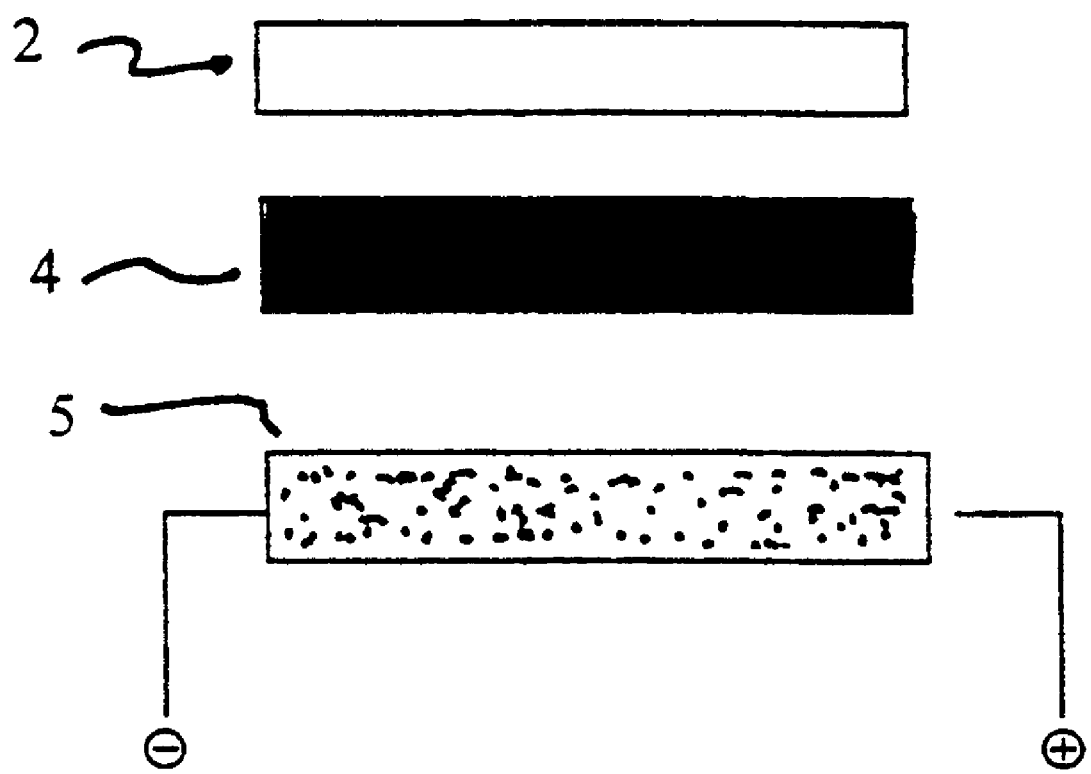
FIG. 5 is a perspective view of a sandwich assay format showing application of an electrical energy source to the second film of the present invention.

Useful solid chemical components of the present invention include acids, bases, salts, enzymes, inorganic or organic catalysts, or electron donor sources. The specific solid chemical component chosen depends largely on the identity of the chemical leaving group X shown in FIGS. 1–3. Referring now to FIG. 1, this schematic depicts a nucleic acid chemiluminescent assay wherein a target DNA molecule is bound to a film. A sensitizer-labeled oligonucleotide probe complimentary in sequence to the target DNA is hybridized to the target DNA. Coating of the film with an olefin reagent, such as that shown in FIG. 3, is then performed. Subsequent to the exposure of the thus coated film to light and oxygen, the sensitizer is promoted to an excited state which allows for transfer of its excess energy to ambient oxygen, with the resultant formation of singlet oxygen. Singlet oxygen reacts with the olefin reagent to form a stable chemiluminescent 1,2-dioxetane, as shown in FIGS. 1–3. When this film is placed in intimate contact with a second film of the present invention, as shown in FIGS. 4 and 5, an activating substance from the solid chemical component on the second film is released by exposure to an energy source for reaction with the stable dioxetane on the first film. Decomposition of the dioxetane subsequently occurs, with the result being a detectable chemiluminescent signal.

Olefins having the structure shown in FIG. 3 have been described in U.S. Pat. No. 5,386,017 to Schaap. Treatment of a stable dioxetane located on a first film with the appropriate activating agent released from a second film of the present invention produces chemiluminesence. The X group on the dioxetane represents a labile leaving group. This group is "activated" or chemically cleaved by the solid chemical component on the second film. Examples of typical X groups which can be removed chemically as well as enzymatically are shown in U.S. Pat. No. 5,795,987. Useful X-oxy protecting groups include, but are not limited to, hydroxyl, alkyl or aryl carboxyl ester, inorganic oxy acid salt, alkyl or aryl silyloxy and oxygen pyranocide. Additional examples of protecting groups as well as the corresponding cleavage/activating agents used for removal of X can also be found in the standard treatise on protecting groups (reference Greene and Vuts, in Protective Groups in Organic Synthesis, 1999).

Table 1 shows several activatable oxide groups (OX), which act as protecting groups on the dioxetane. Table 1 also shows the corresponding solid chemical component or components on the second film of the present invention, which are capable of removing the labile X group of the stable dioxetane to form the signal. The choice of solid chemical component will depend largely on the X group on the dioxetane. In the case of X being hydrogen, deprotonation will be required in order to decompose the dioxetane for signal formation. In such as case, the solid chemical component when exposed to the proper energy source will release a base. For example, the solid chemical component on the second film may be ammonium carbonate, which when exposed to heat liberates a gaseous base ($NH_3$), water, carbon dioxide and, if $NH_3$ reacts with water, hydroxy (OH—) anions. The basic components released then act to deprotonate the dioxetane resulting in signal formation.

The soluble chemical component or components on the second film of the present invention may be deposited thereon by such methods as coating, dipping, spraying, precipitating out of solution, and the like.

When the solid chemical component on the second film is an acid, desirable acids include but are not limited to benzoic acid and p-nitrobenzoic acid. When the solid chemical component on the film is a base, desirable bases include but are not limited to ammonium carbonate, ammonium carbamate, dibasic ammonium phosphate and potassium hydroxide. Useful salts for the solid chemical component include but are not limited to sodium iodide, sodium metaphosphate trihexahydrate and sodium orthophosphate-mono-H dodecahydrate. Where the solid chemical component is a salt, it is desirable that it have a low melting temperature such that exposure to mild heat, e.g., 100° C., causes the salt to be melted and hence, activated and made available for cleavage of the labile groups on the stable dioxetane. In addition, bases released in this manner, when exposed to mild heat conditions may combine with water vapor produced during heating and thereby become activated and available for cleavage of the labile group. Where the solid component is an enzyme, desired enzymes include alkaline phosphatase and horseradish peroxidase. The desirable means of activation of the enzyme would be hydration in the presence of buffering salts.

TABLE 1

| PROTECTING GROUP (OX) on DIOXETANE | CORRESPONDING SOLID CHEMICAL COMPONENT FOR CLEAVING/PROTECTING GROUP |
|---|---|
| Methoxymethyl ether | NaI, Benzoic Acid |
| 2,2 dichloro-1,1-difluoroethyl ether | KOH |
| trimethylsilyl ether | tetrabutylammonium fluoride hydrate |
| hydroxyl | ammonium carbonate |
| acetate ester | sodium carbonate, decahydrate |
| phosphate | alkaline phosphatase, Tris-Cl |

As previously mentioned, the second film includes a solid chemical component which component may be selected from acids, bases, salts, enzymes, inorganic and organic catalysts, and electron donor sources and which is acted upon by an energy source to cause release of an activating substance for production of a chemiluminescent signal on the first target molecule-bound film. This energy source may be chosen from thermal energy, electromagnetic energy, electrical energy, mechanical energy, and combinations thereof. In the case where the solid chemical component is an enzyme, the energy source will be hydration, i.e., exposure to sufficient water to release the buffered enzyme. One embodiment uses thermal energy as the energy source, wherein the energy comprises a temperature of about 30° to 100° C. Where the solid chemical component is a base in salt form with a melting temperature of 100° C. or lower, an application of a temperature of 100° C. or less causes the base to melt and become activated to allow for reactivity with a chemiluminescent precursor compound on another film for production with a chemiluminescent signal. Moreover, an increase in temperature results in the production of water and/or water vapor capable of dissolving a base or other solid component regardless of the melting temperature of the solid component and thereby activating it and making it available for reactivity with a chemiluminescent precursor compound on another film for signal production. Furthermore, production of water vapor upon heating causes formation of a gaseous base in certain instances which can become available for reactivity with a chemiluminescent precursor on another film by diffusion. For example, wherein the base used is ammonium carbonate, heating produces the gaseous base $NH_3$.

In yet another embodiment, an electromagnetic energy source comprised of light having a wavelength about 30 nm to 1,100 nm is envisioned to be useful in the generating of an activating substance on the solid phase of the present invention. An additional energy source embodied by the present invention includes positioning the second film of the invention with another film (e.g., the first film) having a target molecule thereon to create intimate contact therebetween. If necessary, pressure can be applied to create such intimate contact. Such intimate contact allows for diffusion of an activating substance from the second film of the present invention to the first film having a target molecule thereon to allow for production of a chemiluminescent signal.

In one desirable embodiment, the chemiluminescent precursor compound, which reacts with the activating substance released from the second film of the present invention is a stable 1,2-dioxetane, the structure of which is shown in FIG. 3. The preferred 1,2-dioxetane contains a labile chemical group X removable by enzymatic or chemical cleavage by the activating substance, i.e., that which is released from the second chemical component. Such dioxetanes are thermally stable and are known in the art.

In another embodiment, the film of the present invention may further comprise a second chemical component, immobilized on or impregnated within said phase which component when exposed to an energy source maintains the pH of the activating substance within a range sufficient to produce a chemiluminescent signal. In this embodiment, the second solid chemical component may be an acid, base, salt or a combination thereof. For example, wherein the labile group on the dioxetane requires deprotonation by a base, the first solid chemical component on the film of the invention may be the salt ammonium bicarbonate, which when exposed to mild heat, e.g., 80° C., forms water and/or water vapor, with concomitant production of ammonia, carbon dioxide and OH anion. Carbon dioxide, however, is sufficiently acidic to neutralize the basic environment, making deprotonation of the dioxetane less than optimal. It may be desirable, therefore, to include a second chemical component, such as potassium hydroxide, on the film to neutralize the acidic carbon dioxide, such that the pH of the chemical environment is within a range to support optimal cleavage, i.e., about pH 13–14 of the labile group on the stable dioxetane for resultant formation of a signal.

However, it should be noted that even in the absence of a second chemical component such as potassium hydroxide, a high sensitivity of detection was achieved with ammonium bicarbonate as the sole solid chemical component, combined with mild heat with as few as 25 fmoles of target DNA detectable.

When the second solid chemical component is an acid, desirable acids include, but are not limited to, benzoic acid and p-nitrobenzoic acid. When the second solid chemical component is a base, desirable bases include, but are not limited to, sodium hydroxide, potassium hydroxide and sodium carbonate decahydrate. A useful salt for the second solid chemical component includes, but is not limited to sodium sulfate decahydrate.

In one embodiment, the second chemical component is or releases a base wherein the pH is maintained at equal to or about 8. In a preferred embodiment, the second solid chemical component is a base, or a salt which releases a base which together with the first solid chemical component, maintains the pH at about 13 to about 14. The usefulness of this invention is meant to extend to solid-phase immunoassays, as well as nucleic acid assays. Although exposure of an antibody-antigen complex to high pH would normally not be desirable, it is noted that even if the antibody-antigen complex were to dissociate, the ability to detect a signal would not be adversely effected. This is because following exposure of the olefin coated membrane to light and oxygen (air), singlet oxygen is formed which allows for conversion of the olefin to a stable dioxetane, but only in the hybridization zone. Thus, subsequent exposure to base with resulting deprotonation of the dioxetane will yield a signal regardless of whether the antibody-antigen complex remains intact.

Alternatively, wherein the solid chemical component required for activation of the stable dioxetane is an enzyme, the second solid chemical component may be a buffering salt, including but not limited to Tris.Cl which is useful for maintaining the pH within a neutral range as required for maximum catalytic activity of most enzymes.

Referring now to FIG. 4, there is a depiction of a sandwich formation useful for the proper positioning of the two films. Film 4 represents a film having a hybridized target molecule and triggerable dioxetane thereon. Film 5 represents the second film of the present invention which contains the solid chemical component or components. Films 4 and 5 are positioned in overlapping relationship and in intimate contact therebetween. A transparent protective film 3 is positioned between photographic film 2 and film 4. The entire sandwich structure is supported by glass plates 1 and 6, respectively. Energy source 7 is applied to the sandwich format of FIG. 5 to activate and/or release the chemical component needed to react with the stable dioxetane in film 4. As noted above, various types of energy sources are useful. Positioning of photographic film 2 in this manner allows for capture of the chemiluminescent signal. It should be noted, however, that other means of signal detection and capture may be utilized in place of the photographic film. Electronic devices may be useful in this regard. FIG. 5/5 shows application of a voltage to second film 5. This application of electrical energy may serve to apply heat to or cause ion flow in the solid chemical component on film 5.

The following non-limited examples are provided but are not intended to limit the scope or spirit of the invention in any way.

EXAMPLES

Example 1

Sensitizer Labeling of Oligonucleotide

Modified methylene blue derivatives were obtained according to procedures described by Motsenbocker, et al.

The terminal carboxy group of an activated N-hydroxysuccinimido ester form of the methylene blue sensitizer was coupled to a 5'-aminomodified oligonucleotide using standard methods known in the art. (Ruth, J. L., in Oligonucleotides and Analogues: A Practical Approach, Eckstein (Editor), pp. 255–280, Oxford University Press, NY 1991). The oligonucleotide was complementary in sequence to cDNA encoding alcohol dehydrogenase. The 5'-aminomodified oligonucleotides used for labeling with methylene blue as well as unmodified oligonucleotides used for PCR amplification of the target alcohol dehydrogenase cDNA were synthesized on a PE Biosystems Nucleic Acid Synthesizer, Model No. ABI 3948.

Example 2

Dot Blot Hybridization of Methylene Blue-labeled Oligonucleotide to Target DNA

Following PCR amplification of the target DNA, said DNA was spotted on a Hybond+ nylon membrane (Amersham-Pharmacia), along with negative controls of linearized pUC19 DNA at various concentrations ranging from 25 to 500 fmoles in a total volume of 1 microliter. Spots were allowed to dry. The DNA was subsequently denatured and fixed as follows: 1 minute soak in 1.5 M NaCl; 0.5 M NaOH, followed by fixation by baking at 120° C. for 40 minutes, followed by 5 minute soak in 1.5 M NaCl; 0.5 M Tris-Cl pH 7.5. Hybridization was as follows: The filter membrane was soaked in prehybridization buffer (0.25 M Na—$PO_4$; pH 7.2; 7% (w/v) SDS for 45 minutes at 40° C. in a total volume of 0.5 ml per $cm^2$ membrane. The labeled oligonucleotide probe was added directly to the prehybridization buffer at a final concentration of about 2 umoles/ml and incubated for 16 h at 40° C. The hybridized membrane was washed in a buffer of 6×SSC at room temperature for two times at 5 minutes each wash followed by two times at 5 minutes each wash in 3×SSC at 40° C. to remove nonstringent or background hybridization.

Example 3

Method of Detecting Target DNA Hybridized to Methylene Blue-labeled Oligonucleotide Hybridization was detected by first briefly (less than 5 seconds) dipping the hybridized membrane in an olefin solution (1/100% w/v in hexane or methanol), wherein olefin was synthesized by the method of Schaap as described in U.S. Pat. No. 4,857,652, and allowing it to air dry, then illuminating the hybridized surface with red light for 15 minutes. In order to detect the signal, a sheet of filter paper previously soaked in a saturated solution of ammonium carbonate and then dried to a solid form was taped to a glass plate. The hybridized membrane with bound target DNA was subsequently placed (DNA side up) on top of the filter paper containing the dried base and a sheet of plastic was placed on top of this. In the dark, a sheet of Hyperfilm ECL (Amersham-Pharmacia) was placed over the plastic sheet and another glass plate was placed on top. The whole sandwich formation was incubated at 80° C. for 15 minutes to allow for release of the base from the filter paper and resultant activation of the stable chemiluminescent precursor compound present on the hybridized membrane. The film was developed using standard techniques and successful hybridization was observed as black spots on the Hyperfilm ECL with the lowest quantity of DNA detected being in the range of 25 fmoles.

Example 4

Sensitizer Labeling of an Antibody or Antigen

A modified methylene blue derivative is obtained according to procedures described by Motsenbocker, et al. The terminal carboxy group of an activated N-hydroxysuccinimido ester form of the methylene blue sensitizer is coupled to an antibody or antigen via the terminal amino group using standard methods known in the art. The antibody probe used is specific for an antigen target molecule or alternatively, an antigen probe is specific for an antibody target molecule.

Example 5

Dot Blot Hybridization of Methyleneblue-labeled Antibody Probe to Target Antigen Molecules Antigen is spotted on a nitrocellulose, PVDF or nylon membrane in various concentrations. The membrane is subsequently blocked in a solution of 0.2% casein/0.1% Tween 20 detergent in aqueous phosphate buffered saline solution (PBS) for 1 hour, following which a 1/2000 to 1/5000 dilution of methylene blue-labeled antibody in 0.2% casein in PBS is added, wherein the antibody is specific for the target antigen molecule. The membrane is then incubated for 1 hour at room temperature and washed five times (for 5 minutes each time) in 0.3% Tween 20 detergent in PBS, and one time in PBS at room temperature for 5 minutes to remove non-specific or non-stringent binding.

Example 6

Method of Detecting Target Antigen Hybridized to Methylene Blue-labeled Antibody Hybridization is detected by first briefly (less than 5 seconds) dipping the hybridized membrane in an olefin solution (1/100% w/v in hexane or methanol and allowing it to air dry, then illuminating the hybridized surface with red light for 15 minutes. In order to detect the signal, a sheet of filter paper previously soaked in a saturated solution of ammonium carbonate and then dried to a solid form is taped to a glass plate. The hybridized membrane with bound target antigen is subsequently placed (antigen side up) on top of the filter paper containing the dried base and a sheet of plastic is placed on top of this. In the dark, a sheet of Hyperfilm ECL (Amersham-Pharmacia) is placed over the plastic sheet and another glass plate is placed on top. The whole sandwich formation is incubated at 80° C. for 15 minutes to allow for release of the base from the filter paper and resultant activation of the stable chemiluminescent precursor compound present on the hybridized membrane. The film is developed using standard techniques for signal detection.

What is claimed is:

1. A film for use in chemiluminescent assays comprising at least one solid chemical component immobilized on or impregnated therewith which when acted upon by an energy source releases an activating substance, which substance in the presence of a chemiluminescent precursor compound reacts therewith to produce a chemiluminescent signal for the detection of a target molecule.

2. A film according to claim 1 wherein said film comprises a polymeric film.

3. A film according to claim 1 wherein said film further comprises a textile, paper or cellulose film.

4. A film according to claim 1 wherein said solid chemical component is selected from the group consisting of acids, bases, salts, enzymes, inorganic and organic catalysts, and electron donor sources.

5. A film according to claim 1 wherein said solid chemical component is an acid selected from the group consisting of benzoic acid and p-nitrobenzoic acid.

6. A film according to claim 1 wherein said solid chemical component is a base selected from the group consisting of ammonium carbonate, ammonium carbamate, dibasic ammonium phosphate and potassium hydroxide.

7. A film according to claim 1 wherein said solid chemical component is a salt selected from the group consisting of sodium iodide, sodium metaphosphate trihexahydrate, sodium orthophosphate-mono-H dodecahydrate.

8. A film according to claim 1 wherein said energy source is selected from the group consisting of thermal energy, electromagnetic energy, electrical energy, mechanical energy and combinations thereof.

9. A film according to claim 1 wherein said energy source comprises a temperature of about 30° to about 100° C.

10. A film according to claim 1 wherein said electromagnetic energy source comprises light having a wavelength from about 30 nm to about 1,100 nm.

11. A film according to claim 1 wherein said mechanical energy comprises application of pressure to said film to create intimate contact with another film having a target molecule thereon.

12. A film according to claim 1 wherein said chemiluminescent precursor compound is a 1,2-dioxetane.

13. A film according to claim 12 wherein the 1,2-dioxetane contains a labile chemical group removable by chemical or enzymatic cleavage by said activating substance.

14. A film according to claim 12 wherein the 1,2 dioxetane is formed from an olefin.

15. A film according to claim 14 wherein the olefin is covalently bound to a fluorescent molecule which further enhances chemiluminescent detection.

16. A film according to claim 1 wherein said film further comprises a second solid chemical component immobilized on or impregnated within said film which component when exposed to said energy source maintains the pH of said activating substance within a range sufficient to produce a chemiluminescent signal.

17. A film according to claim 16 wherein said second solid chemical component is selected from the group consisting of acids, bases, salts and combinations thereof.

18. A film according to claim 16 wherein said second solid chemical component is an acid selected from the group consisting of benzoic acid, p-nitrobenzoic acid.

19. A film according to claim 16 wherein said second solid chemical component is a base selected from the group consisting of sodium hydroxide, potassium hydroxide, sodium carbonate decahydrate.

20. A film according to claim 16 wherein said second chemical component is the salt sodium sulfate decahydrate.

21. A film according to claim 16 wherein said second solid chemical component is or releases a base and wherein said pH is equal to about 8.

22. A film according to claim 16 wherein said second solid chemical component is or releases a base and wherein said pH is 13–14.

23. A film for use in the detection of a target molecule in solid-phase and gel chemiluminescent assays comprising first and second solid chemical components immobilized on or impregnated within a film or membrane which components when acted upon by an energy source together allow for release of an activating substance at a pH sufficient to produce a chemiluminescent signal upon reaction of said activating substance with a chemiluminescent precursor compound.

24. A film for use in chemiluminescent assays comprising at least one solid chemical component immobilized on or impregnated therein which when hydrated releases an activating substance, which substance in the presence of a chemical precursor compound reacts therewith to produce a chemiluminescent signal for the detection of a target molecule.

25. A film according to claim 24 wherein said film comprises a polymeric film.

26. A film according to claim 25 wherein said film comprises a textile or cellulose film.

27. A film according to claim 24 wherein said solid chemical component is an enzyme.

28. A film according to claim 24 wherein said solid chemical component is an enzyme selected from the group consisting of alkaline phosphatase and horseradish peroxidase.

29. A film according to claim 24 wherein said chemiluminescent precursor compound is a 1,2 dioxetane.

30. A film according to claim 29 wherein said dioxetane contains a labile group removable by enzymatic cleavage.

31. A film according to claim 24 wherein said film further comprises a second solid chemical component immobilized on or impregnated within said film which when exposed to hydration maintains the pH of said activating substance within a range sufficient to produce a chemiluminescent signal.

32. A film according to claim 23 wherein said second solid chemical component is selected from the group consisting of acids, bases, salts and combinations thereof.

33. A film according to claim 23 wherein said second solid chemical component is Tris.Cl.

34. A method of detecting target molecules using chemiluminescence comprising the steps of:
   (a) providing a first film having a complex comprising a target molecule bound to a sensitizer labeled probe;
   (b) providing a second film comprising at least one solid chemical component immobilized on or impregnated on said film, which chemical component when acted upon by an energy source releases an activating substance which in the presence of a chemiluminescent precursor compound reacts therewith to produce a chemiluminescent signal for the detection of a target molecule;
   (c) contacting said complex with an olefin reagent to place said complex and said olefin reagent in reactive proximity to each other;
   (d) exposing said complex to light and oxygen to create a chemiluminescent precursor compound;
   (e) contacting said first film with said second film and allowing said second film to be acted upon by an energy source to allow release from said second film of an activating substance which in the presence of said chemiluminescent precursor compound reacts to produce a chemiluminescent signal for the detection of said target molecules; and
   (f) detecting and/or recording said resultant chemiluminescent signal.

35. The method of claim 34 wherein the second film is a polymeric, textile, paper or cellulose film.

36. The method of claim 34 wherein said solid chemical component is selected from the group consisting of acids, bases, salts, enzymes inorganic catalysts and organic catalysts.

37. The method of claim 34 wherein said solid chemical component is benzoic acid or p-nitrobenzoic acid.

38. The method of claim 34 wherein said chemical component is ammonium carbonate, ammonium carbamate, dibasic ammonium phosphate, potassium hydroxide and combinations thereof.

39. The method of claim 34 wherein said solid component is an enzyme selected from the group consisting of alkaline phosphatase and horseradish peroxidase.

40. The method of claim 34 wherein said solid chemical component is an enzyme and said energy source is hydration.

41. A chemiluminescent assay kit comprising:
(1) a first film for binding of a target molecule thereon;
(2) a second film comprising at least one solid chemical component immobilized on or impregnated within said film, which chemical component when acted upon by an energy source releases an activating substance which in the presence of a chemiluminescent precursor compound reacts therewith to produce a chemiluminescent signal for the detection of a target molecule.

42. The assay kit of claim 41 further including a buffer solution suitable for hybridization of proteins.

43. The assay kit of claim 41 further including a buffer solution for hybridization of antibodies or antigens.

44. The assay kit of claim 41 further including a buffer solution for hybridization of nucleic acids.

45. The assay kit of claim 41 further including a buffer solution suitable for blocking of proteins.

46. The assay kit of claim 41 further including a buffer solution suitable for pre-hybridization of nucleic acids.

47. The assay kit of claim 41 further including a washing buffer solution for proteins.

48. The assay kit of claim 41 further including a washing buffer solution for nucleic acids.

49. The assay kit of claim 41 wherein said solid chemical component is selected from the group consisting of acids, bases, salts, enzymes, inorganic catalysts, organic catalysts and combinations thereof.

50. The assay kit of claim 41 wherein said solid chemical component is a base selected from the group consisting of ammonium carbonate, ammonium carbamate, dibasic ammonium phosphate, potassium hydroxide and combinations thereof.

51. The assay kit of claim 41 further including an activated ester form of a sensitizer for reaction with proteins and aminomodified oligonucleotides.

52. The method of claim 41 wherein said solid chemical component is an enzyme and said energy source is hydration.

53. A method of preparing a chemiluminescent assay comprising the steps of:
(1) providing a first film having bound thereon target molecules, wherein said bound target molecules have been subjected to a pre-hybridization or blocking buffer solution under temperatures suitable for a chosen probe and wherein said film is further incubated with hybridization solution containing said probe under conditions suitable to bind said probe and wherein said film is exposed to an olefin solution;
(2) providing a second film by immobilizing on or impregnating therein at least one solid chemical component which when acted upon by an energy source releases an activating substance and further which in the presence of a chemiluminescent precursor compound reacts therewith to produce chemiluminescent signal for the detection of a target molecule;
(3) positioning said first and second films in overlapping contact with each other to permit release of an activating substance from said second film and reaction with said chemiluminescent precursor compound on said first film to result in a detectable chemiluminescent signal.

54. The method of claim 53 wherein prior to positioning said first and second films in overlapping relationship, said first film is exposed to sufficient light and oxygen to form a stable chemiluminescent precursor compound.

55. The method of claim 53 wherein said stable chemiluminescent precursor compound is formed from the transfer of energy from said sensitizer molecules to ambient molecular oxygen with the resultant formation of singlet oxygen, said singlet oxygen subsequently reacting with said olefin to form said stable chemiluminescent precursor compound.

56. The method of claim 53 wherein said first and second films positioned in overlapping relationship are placed proximate to a detection device for capture of said chemiluminescent signal.

57. The method of claim 53 wherein said detection device is x-ray film or photographic film.

58. The method of claim 53 wherein said device is an electronic sensing device.

* * * * *